United States Patent
Kriegbaum

(10) Patent No.: US 9,216,994 B2
(45) Date of Patent: Dec. 22, 2015

(54) PROCESS FOR PREPARING BENZO[1,2-B;4,5-B']DITHIOPHENE-4,8-DICARBOXYLIC ACID OR ITS 2,3-DIHYDRO DERIVATIVE

(71) Applicant: Merck Patent GmbH, Darmstadt (DE)

(72) Inventor: Eva Kriegbaum, Pfungstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/385,775

(22) PCT Filed: Feb. 25, 2013

(86) PCT No.: PCT/EP2013/000538
§ 371 (c)(1),
(2) Date: Sep. 17, 2014

(87) PCT Pub. No.: WO2013/139426
PCT Pub. Date: Sep. 26, 2013

(65) Prior Publication Data
US 2015/0051409 A1    Feb. 19, 2015

(30) Foreign Application Priority Data
Mar. 21, 2012  (EP) .................................... 12001990

(51) Int. Cl.
*C07D 495/04* (2006.01)
*C07D 405/04* (2006.01)

(52) U.S. Cl.
CPC ............ *C07D 495/04* (2013.01); *C07D 405/04* (2013.01)

(58) Field of Classification Search
CPC ................................................... C07D 495/04
USPC ............................................................. 549/43
See application file for complete search history.

(56) References Cited

U.S. PATENT DOCUMENTS

| 5,202,440 A | 4/1993 | Desai |
| 2014/0061538 A1 | 3/2014 | Blouin et al. |

FOREIGN PATENT DOCUMENTS

| CN | 1032440 A | 4/1989 |
| WO | 9422871 A | 10/1994 |
| WO | 9611929 A | 4/1996 |
| WO | 2012156022 A1 | 11/2012 |

OTHER PUBLICATIONS

International Search Report from PCT/EP2013/000538 dated Apr. 24, 2013.
Attilio Citterio et al. "Oxidative Dimerization of Diethyl 3-Thienylmalonate by High Valent Metal Salts, Synthesis of Benzo[1,2-b']dithiophene Derivatives" Tetrahedron, [1996], vol. 52, No. 41, pp. 13227-13242.
MM. Michel Hebert et al. "Synthesis and reactivity of 4,8-diformylbenzo [1,2-b;4,5-b']dithiophene", Compte Rendus Des Seances De L' Academie Des Sciences, Serie C: Sciences Chimiques, Elsevier, [1971], vol. 273, No. 21, pp. 1451-1453. (Need English)!!!!!!!!!!!!!!!!!!
English Translation of Chinese Office Action 201380014171.3 dated Oct. 22, 2015.

*Primary Examiner* — Taofiq A Solola
(74) *Attorney, Agent, or Firm* — Millen, White, Zelano and Branigan, P.C.

(57) ABSTRACT

The invention relates to a process for preparing benzo[1,2-b;4,5-b']dithiophene-4,8-dicarboxylic acid or its 2,3-dihydro derivative, and to novel products prepared by this process.

7 Claims, No Drawings

PROCESS FOR PREPARING BENZO[1,2-B;4,5-B']DITHIOPHENE-4,8-DICARBOXYLIC ACID OR ITS 2,3-DIHYDRO DERIVATIVE

The invention relates to a process for preparing benzo[1,2-b;4,5-b']dithiophene-4,8-dicarboxylic acid or its 2,3-dihydro derivative, and to novel products prepared by this process.

Benzo[1,2-b:4,5-b']dithiophene (hereinafter shortly referred to as "BDT") which is substituted in 4- and 8-position, has been found to be especially suitable as electron donor unit in conjugated polymers and copolymers which are used as semiconductor in organic electronic (OE) devices like organic photovoltaic (OPV) cells or organic field effect transistors (OFET).

The addition of substituents like alkyl or carboxyl groups in 4- and 8-position of the BDT core leads to improved solubility and electronic properties of the polymer, enabling OE devices to be manufactured by solution-processing techniques like spin casting, dip coating or ink jet printing. Solution processing can be carried out cheaper and on a larger scale compared to the evaporative techniques that are typically used to make inorganic electronic devices.

When used in OPV devices, especially in bulk heterojunction (BHJ) photovoltaic devices, the conjugated polymer serves as the main absorber of the solar energy and should have a low band gap to absorb the maximum of the solar spectrum. It was found that by incorporation of an electron-donating BDT unit and an electron-accepting unit into a copolymer i.e. a "donor-acceptor" polymer, a reduction of the bandgap can be achieved, which enables improved light harvesting properties.

When used as semiconductor in the active channel of an OFET, polymers and copolymers incorporating BDT units were shown to have high charge carrier mobility and low conductivity in the off state, enabling high current on/off ratios. In addition, they have a high ionisation potential and thus are relatively stable to oxidation which could reduce device performance.

BDT units with carboxyl substituents in 4- and 8-position show especially promising properties, for example as electron donating group in conjugated semiconducting polymers, and have been shown to yield OPV devices with high power conversion efficiency and OFET devices with high charge carrier mobility.

A key intermediate in the synthesis of 4,8-dicarboxyl BDT monomeric units is benzo[1,2-b:4,5-b']dithiophene-4,8-dicarboxylic acid:

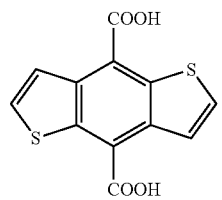 [SMILES: O=C(O)c1c2ccsc2c(C(=O)O)c2ccsc12]

Citterio, A.; Sebastiano, R.; Maronati, A.; Viola, F.; Farine, A. *Tetrahedron* 1996, 13227-13242 report the synthesis of benzo[1,2-b;4,5-b']dithiophene-4,8-dicarboxylic acid 3 starting from tetra ethyl ester 1 in two steps, as illustrated in Scheme 1 below. Radical initiated de-esterification of compound 1 results in the aromatisation and formation of the benzo-dithiophene diester 2, which upon hydrolysis with KOH in dioxane leads to the formation of dicarboxlic acid 3. Citterio et al. also report that the tetra ester 1 can be transformed into benzo[1,2-b:4,5-b']dithiophene-4,8-dicarboxylic acid 3 in one step upon treatment with KOH in dioxane followed by acidification with HCl in the presence of oxygen.

Scheme 1

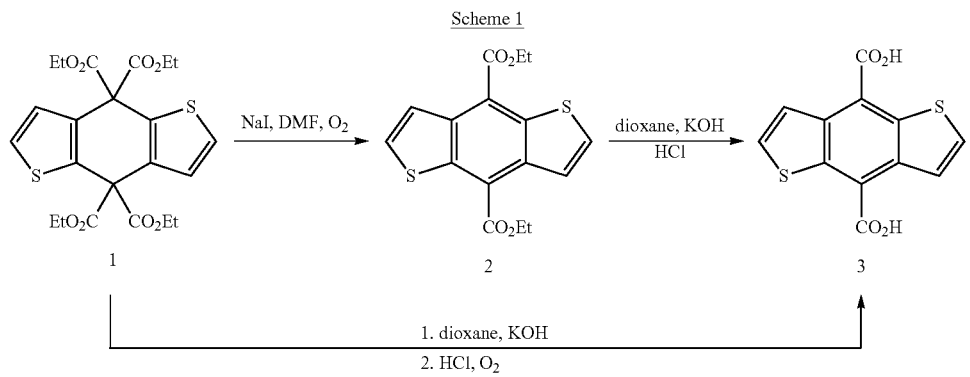 [SMILES: CCOC(=O)C1(C(=O)OCC)c2ccsc2C(C(=O)OCC)(C(=O)OCC)c2ccsc21 ; CCOC(=O)c1c2ccsc2c(C(=O)OCC)c2ccsc12 ; Cl ; O=C(O)c1c2ccsc2c(C(=O)O)c2ccsc12]

However, the inventors of the present invention have found that the literature reported two-step synthesis of dicarboxylic acid 3 from tetra ethyl ester 1 could be reproduced only with lower yield than reported and moderate purity, whereas the one step version with dioxane and KOH always led to an inseparable mixture of desired dicarboxylic acid 3 and the dihydrothiophene analogue 4 as shown in Scheme 2, regardless of the reaction conditions.

Scheme 2

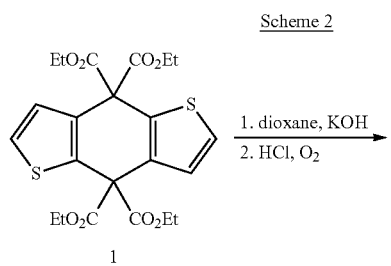

-continued

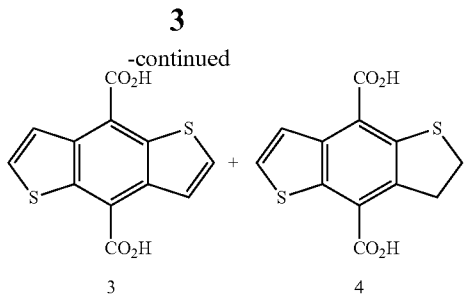

Furthermore the reaction turned out to be non-scalable. The larger the reaction scale, the worse the product: side product ratio obtained, even though oxygen (2% in $N_2$) was bubbled through the reaction mixture.

For industrial production it is essential to provide a reaction path that allows synthesis at large scale in satisfying yield and purity, without or only with low amounts of undesired side products It was therefore an aim of the present invention to provide a process for the synthesis of benzo[1,2-b;4,5-b']dithiophene-4,8-dicarboxylic acid that does not have the drawbacks of the synthesis methods described in prior art, allows synthesis in satisfying yield and purity without or only with reduced amount of side products, and is especially suitable for synthesis at large scale.

The inventors of the present invention have found that these aims could be achieved by providing a process as described and claimed hereinafter.

The invention relates to a process for preparing benzo[1,2-b;4,5-b']dithiophene-4,8-dicarboxylic acid or its 2,3-dihydro derivative, by A) heating benzo[1,2-b;4,5-b']dithiophene-4,4,8,8-tetracarboxylic acid, or and acid derivative thereof, in an organic solvent in the presence of a base and an oxidising agent, and adding an acid, to give benzo[1,2-b;4,5-b']dithiophene-4,8-dicarboxylic acid, or B) heating benzo[1,2-b;4,5-b']dithiophene-4,4,8,8-tetracarboxylic acid, or an acid derivative thererof, in a polar organic solvent in the presence of a base under exclusion of an oxidising agent, and adding an acid, to give 2,3-dihydrobenzo[1,2-b;4,5-b']dithiophene-4,8-dicarboxylic acid.

Alternatively to the benzo[1,2-b;4,5-b']dithiophene-4,4,8,8-tetracarboxylic acid, an acid derivative thereof can also be used as educt, for example an ester like the corresponding tetraalkyl or tetraaryl ester, or an amide. A suitable and preferred tetraalkyl ester is for example tetraethyl ester as shown in Scheme 3 below.

The benzo[1,2-b;4,5-b']dithiophene-4,4,8,8-tetracarboxylic acid or acid derivative can also be substituted in one or more of the 2-,3-, 6- or 7-position, for example by alkyl or aryl groups.

In a preferred embodiment the benzo[1,2-b;4,5-b']dithiophene-4,4,8,8-tetracarboxylic acid or acid derivative is substituted in one or more of the 2-,3-, 6- or 7-positions by a substituent $R^1$, wherein $R^1$ is selected from F, Cl, Br, I, CN, $R^2$, —C(O)—$R^2$, —O—C(O)—$R^2$, —$SO_2$—$_{R^2}$ or —$SO_3$—$R^2$, wherein $R^2$ is straight-chain, branched or cyclic alkyl with 1 to 30 C atoms, in which one or more non-adjacent C atoms are optionally replaced by —O—, —S—, —C(O)—, —O—C(O)—O—, —$SO_2$—, —$SO_3$—, —CH=CH— or —C≡C— and in which one or more H atoms are optionally replaced by F, Cl, Br, I or CN, or $R^2$ is aryl or heteroaryl having 4 to 30 ring atoms which is unsubstituted or substituted by one or more halogen atoms or by one or more groups selected from alkyl, alkoxy, sulfanylalkyl, sulfonylalkyl, alkylcarbonyl, each having 1 to 20 C atoms and each being optionally fluorinated.

The invention further relates to the compound 2,3-dihydrobenzo[1,2-b;4,5-b']dithiophene-4,8-dicarboxylic acid, which is optionally substituted in one or more of the 2-,3-, 6- or 7-positions by a substituent $R^1$ as defined above. This compound can be formed in quantitative yield by the process according to the present invention, but was hitherto not available.

The process of the present invention is exemplarily shown in Scheme 3, without intending to restrict the invention.

Scheme 3

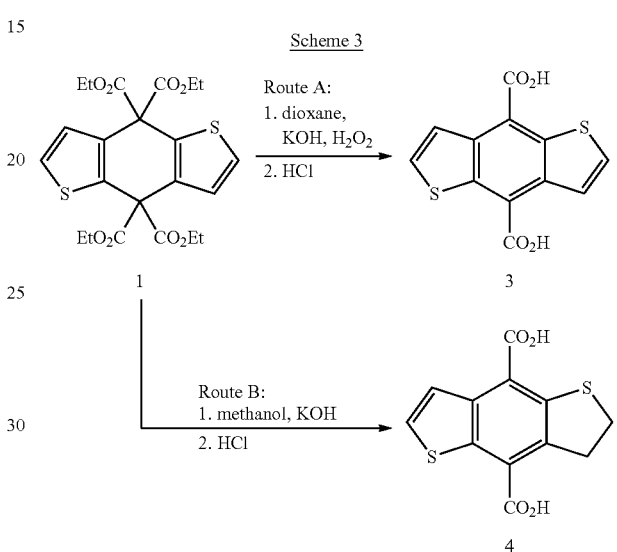

The process enables the quantitative formation of either benzo[1,2-b;4,5-b']dithiophene-4,8-dicarboxylic acid 3, or 2,3-dihydro-benzo[1,2-b;4,5-b']dithiophene-4,8-dicarboxylic acid 4, from the benzo[1,2-b;4,5-b']dithiophene-4,4,8,8-tetracarboxylic acid or its alkyl ester 1.

By the correct choice of the reaction conditions the reaction can be directed in either way.

Following route A), upon addition of an oxidising agent the side reaction process, i.e. the mono-reduction of the thiophene ring under formation of dihydrothiophene 4, is suppressed, and instead the desired dicarboxylic acid 3 is formed in quantitative yield.

It is preferred, in particular for large scale processes, to carry out the first reaction step in route A) (before the addition of the acid) in the absence of water, for example by using a peroxide adduct like urea hydrogen peroxide instead of aqueous hydrogen peroxide. However, especially for small or medium scale processes aqueous hydrogen peroxide may also be used as oxidising agent.

Alternatively, following route B) the reaction can be driven quantitatively towards 2,3-dihydro-benzo[1,2-b;4,5-b']dithiophene-4,8-dicarboxylic acid 4 when run in a polar solvent like methanol and under exclusion of an oxidising reagent.

Suitable and preferred solvents for route A) are linear or cyclic alkyl ethers like dioxane, tetrahydrofurane or methyl-tert-butylether, or mixtures thereof.

Suitable and preferred solvents for route B) are alcoholic solvents or mixtures thereof, preferably alkyl alcohols, very preferably $C_1$-$C_4$ alkyl alcohols, for example methanol, ethanol, 2-propanol or tert-butanol. Preferably the reaction in route B) is carried out in a protic medium.

Suitable and preferred oxidising agents in route A) are selected from peroxides or adducts thereof, perborates and percarbonates, like for example hydrogen peroxide, urea hydrogen peroxide, and alkali perborates or alkali percarbonates like sodium perborate or sodium percarbonates. The oxidising agent is usually added until complete conversion is observed.

The reaction mixture in both route A and B is heated to a temperature above room temperature, preferably to a temperature of at least 50° C. At this temperature an intermediate is formed, which reacts to the desired product 3 if an oxidising agent is present as in route A. If no oxidising agent is present as in route B, the intermediate reacts to the dihydro product 4 in a protic medium.

The heating step is preferably carried out in an inert reaction atmosphere like $N_2$.

The base is preferably an alkali hydroxide, like KOH or NaOH.

After the oxidation reaction, the reaction mixture is acidified by adding an acid, preferably an inorganic acid like for example HCl, that protonates the carboxylic group to give the desired carboxylic acid 3 or 4. If an aqueous inorganic acid like $HCl/H_2O$ is used, the water contained therein aids the precipitation of the product.

The product can then be isolated from the reaction mixture and purified by standard work up procedures that are well known to the skilled person and described in the literature, like extraction, filtering, washing, drying etc.

Unless stated otherwise, above and below all percentages of solids are per cent by weight ("wt. %"), all temperatures are given in degrees Celsius (° C.), "room temperature (RT)" means 20° C., and all physical properties and values refer to a temperature of 20° C.

The invention will now be described in more detail by reference to the following examples, which are illustrative only and do not limit the scope of the invention.

EXAMPLE 1

Benzo[1,2-b;4,5-b']dithiophene-4,8-dicarboxylic acid was prepared as follows:

Benzo[1,2-b;4,5-b']dithiophene-4,4,8,8-tetracarboxylic acid tetraethyl ester (20g) was suspended in dioxane (600g) and KOH (75g) under inert atmosphere and heated to 40° C. Hydrogenperoxide (8.6 g; w=35%) was added and the suspension heated at 50° C. for 3 hours. The reaction mixture was acidified with 2M HCl (730 g) and the yellow precipitate filtered off, washed with water and dried in vacuum to yield benzo[1,2-b;4,5-b']dithiophene-4,8-dicarboxylic acid (10,1 g) in 86% yield.

$^1$H-NMR (400 MHz, DMSO): δ=8.27 (d, 1 H), 8.03 (d, 1 H).

EXAMPLE 2

Benzo[1,2-b;4,5-b']dithiophene-4,8-dicarboxylic acid was prepared on larger scale as follows:

Benzo[1,2-b;4,5-b']dithiophene-4,4,8,8-tetracarboxylic acid tetraethyl ester (95 g) was suspended in dioxane (2850 g) and KOH (356 g) under inert atmosphere and heated to 50° C. Hydrogenperoxide (111 g; w=35%) was added in portions over 3.5 hours and the suspension heated at 50° C. for 20 hours. The reaction mixture was acidified with 2M HCl (3500 g) and the yellow precipitate filtered off, washed with water and dried in vacuum to yield benzo[1,2-b;4,5-b']dithiophene-4,8-dicarboxylic acid (50.6 g) in 92% yield.

EXAMPLE 3

2,3-Dihydro-benzo[1,2-b;4,5-b']dithiophene-4,8-dicarboxylic acid was prepared as follows:

Benzo[1,2-b;4,5-b']dithiophene-4,4,8,8-tetracarboxylic acid tetraethyl ester (2 g) was suspended in methanol (60 g) and KOH (7.5 g) under inert atmosphere and heated to reflux for 5 hours. The reaction mixture was acidified with 2M HCl (62.5 g) and the yellow precipitate filtered off, washed with water and dried in vacuum to yield 2,3-dihydro-benzo[1,2-b;4,5-b']dithiophene-4,8-dicarboxylic acid in quantitative yield.

$^1$H-NMR (400 MHz, DMSO): δ=7.96 (d, 1 H), 7.85 (d, 1 H), 3.73 (t, 2H), 3.29 (t, 2H).—$^1$H-NMR (400MHz, THF): δ=8.08 (d, 1H), 7.61 (d, 1H), 3.81 (t, 2H), 3.24 (t, 2H).—HRMS (ESI) m/z: 281 [M+H]$^+$.

The invention claimed is:

1. A process of preparing benzo[1,2-b;4,5-b']dithiophene-4,8-dicarboxylic acid or its 2,3-dihydro derivative, comprising
   A) heating benzo[1,2-b;4,5-b']dithiophene-4,4,8,8-tetracarboxylic acid ester in an organic solvent that is a linear or cyclic alkyl ether, in the of a base, and of an oxidizing agent that is a peroxide, perborate or percarbonate, and adding an inorganic acid, to give benzo[1,2-b;4,5-b']dithiophene-4,8-dicarboxylic acid, or
   B) heating benzo[1,2-b;4,5-b']dithiophene-4,4,8,8-tetracarboxylic acid, or ester derivative, in a polar organic solvent that is a $C_{1-4}$-alkyl alcohol, in the presence of a base under exclusion of an oxidising agent, and adding an acid, to give 2,3-dihydrobenzo[1,2-b;4,5-b']dithiophene-4,8-dicarboxylic acid.

2. The process according to claim 1, wherein the oxidizing agent in route A) is hydrogen peroxide, urea hydrogen peroxide, sodium perborate or sodium percarbonate.

3. The process according to claim 1, wherein the solvent in route A) is dioxane.

4. The process according to claim 1, wherein in route A) heating before addition of the acid is carried out in the absence of water.

5. The process according to claim 1, wherein the heating is carried out in an inert atmosphere.

6. The process according to claim 1, wherein the base is KOH or NaOH.

7. The process according to claim 1, wherein the benzo[1,2-b;4,5-b']dithiophene-4,4,8,8-tetracarboxylic acid acid or ester is substituted in one or more of the 2-,3-, 6- or 7-positions by a substituent $R^1$, wherein $R^1$ is selected from F, Cl, Br, I, CN, $R^2$, —C(O)—$R^2$, —O—C(O)—$R^2$, —$SO_2$—$R^2$ or —$SO_3$—$R^2$, wherein $R^2$ is straight-chain, branched or cyclic alkyl with 1 to 30 C atoms, in which one or more non-adjacent C atoms are optionally replaced by —O—, —S—, —C(O)—, —O—C(O)—O—, —$SO_2$—, —$SO_3$—, —CH=CH— or —C≡C— and in which one or more H atoms are optionally replaced by F, Cl, Br, I or CN, or $R^2$ is aryl or heteroaryl having 4 to 30 ring atoms which is unsubstituted or substituted by one or more halogen atoms or by one or more of optionally F-substituted alkyl, alkoxy, sulfanylalkyl, sulfonylalkyl or alkylcarbonyl, each having 1 to 20 C atoms.

* * * * *